(12) United States Patent
Purwar et al.

(10) Patent No.: US 11,633,148 B2
(45) Date of Patent: *Apr. 25, 2023

(54) SYSTEMS AND METHODS FOR HAIR ANALYSIS

(71) Applicant: The Procter & Gamble Company, Cincinnati, OH (US)

(72) Inventors: Ankur Purwar, Singapore (SG); Faiz Feisal Sherman, Mason, OH (US); Raghunandan Melkote Kainkaryam, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 33 days.

This patent is subject to a terminal disclaimer.

(21) Appl. No.: 17/386,580

(22) Filed: Jul. 28, 2021

(65) Prior Publication Data

US 2021/0353215 A1 Nov. 18, 2021

Related U.S. Application Data

(63) Continuation of application No. 16/441,749, filed on Jun. 14, 2019, now Pat. No. 11,172,873, which is a (Continued)

(51) Int. Cl.
*A61B 5/00* (2006.01)
*G06Q 30/0601* (2023.01)
(Continued)

(52) U.S. Cl.
CPC ............ *A61B 5/448* (2013.01); *A45D 44/005* (2013.01); *A61B 5/0077* (2013.01); *G06N 3/02* (2013.01);
(Continued)

(58) Field of Classification Search
CPC .... A61B 5/448; A61B 5/0077; A45D 44/005; A45D 2044/007; G06N 3/02;
(Continued)

(56) References Cited

U.S. PATENT DOCUMENTS 2,946,725 A 7/1960 Norris
3,070,510 A 12/1962 Cooley
(Continued)

FOREIGN PATENT DOCUMENTS

CN 104586362 A 5/2015
CN 105441213 A 3/2016
(Continued)

OTHER PUBLICATIONS

Chao Sun et al. "Hairstyle Pattern Recognition based on CNNs", IEEE International Conference on Systems, Man, and Cybernetics (SMC), Oct. 5-8, 2017, pp. 1840-1845.
(Continued)

*Primary Examiner* — Stephen P Coleman
(74) *Attorney, Agent, or Firm* — David M Weirich

(57) ABSTRACT

Disclosed are hair analysis systems and methods comprising: (a) capturing an image of a user at as captured by a camera and sending the image to a hair analysis processor; (b) analyzing the user's hair condition at the hair analysis processor, based on the image from the camera by using a model that is trained using a plurality of images of users that each feature one or more micro features of a respective user's hair, and providing an analysis result to a display; and (c) displaying at the display the analysis result to the user. The present invention provides the system and the method with an improved sensitivity.

14 Claims, 2 Drawing Sheets

Related U.S. Application Data continuation of application No. PCT/US2019/032382, filed on May 15, 2019.

(60) Provisional application No. 62/672,583, filed on May 17, 2018.

(51) Int. Cl.
  *G06N 3/02* (2006.01)
  *A45D 44/00* (2006.01)
  *G06T 7/00* (2017.01)

(52) U.S. Cl.
  CPC ... *G06Q 30/0631* (2013.01); *A45D 2044/007* (2013.01); *G06T 7/0012* (2013.01); *G06T 2207/20081* (2013.01); *G06T 2207/20084* (2013.01)

(58) Field of Classification Search
  CPC .... G06N 3/0454; G06N 3/08; G06Q 30/0631; G06T 7/0012; G06T 2207/20081; G06T 2207/20084
  USPC .......................................................... 382/100
  See application file for complete search history.

(56) References Cited

U.S. PATENT DOCUMENTS

| | | | |
|---|---|---|---|
| 3,429,963 A | 2/1969 | Shedlovsky | |
| 3,506,720 A | 4/1970 | Model et al. | |
| 3,535,421 A | 10/1970 | Briner | |
| 3,538,230 A | 11/1970 | Pader | |
| 3,678,154 A | 7/1972 | Widder | |
| 3,689,637 A | 9/1972 | Pader | |
| 3,696,191 A | 10/1972 | Weeks | |
| 3,711,604 A | 1/1973 | Colodney et al. | |
| 3,737,533 A | 6/1973 | Moon et al. | |
| 3,862,307 A | 1/1975 | Di Giulio | |
| 3,911,104 A | 10/1975 | Harrison | |
| 3,935,306 A | 1/1976 | Roberts et al. | |
| 3,959,458 A | 5/1976 | Agricola | |
| 3,988,443 A | 10/1976 | Ploger et al. | |
| 3,991,177 A | 11/1976 | Vidra et al. | |
| 4,040,858 A | 8/1977 | Wason | |
| 4,051,234 A | 9/1977 | Gieske | |
| 4,058,595 A | 11/1977 | Colodney | |
| 4,138,477 A | 2/1979 | Gaffar | |
| 4,154,815 A | 5/1979 | Pader | |
| 4,183,914 A | 1/1980 | Gaffar | |
| 4,304,766 A | 12/1981 | Chang | |
| 4,355,022 A | 10/1982 | Rabussay | |
| 4,590,066 A | 5/1986 | Parran, Jr. et al. | |
| 4,627,977 A | 12/1986 | Gaffar | |
| 4,661,341 A | 4/1987 | Benedict et al. | |
| 4,846,650 A | 7/1989 | Benedict et al. | |
| 4,877,603 A | 10/1989 | Degenhardt | |
| 4,980,153 A | 12/1990 | Jackson et al. | |
| 4,992,420 A | 2/1991 | Neeser | |
| 5,000,939 A | 3/1991 | Dring et al. | |
| 5,037,637 A | 8/1991 | Gaffar et al. | |
| 5,626,838 A | 5/1997 | Cavanaugh, Jr. | |
| 5,827,505 A | 10/1998 | Hughes et al. | |
| 5,939,052 A | 8/1999 | White, Jr. et al. | |
| 6,251,372 B1 | 6/2001 | Witt et al. | |
| 6,707,929 B2 | 3/2004 | Marapane | |
| 7,079,158 B2 | 7/2006 | Lambertsen | |
| 7,104,800 B2 | 9/2006 | Ortiz-valero | |
| 7,435,794 B2 | 10/2008 | Lukyanov et al. | |
| 7,437,344 B2 | 10/2008 | Peyrelevade | |
| 7,964,579 B2 | 6/2011 | Mehta et al. | |
| 8,119,162 B2 | 2/2012 | Miksa | |
| 8,168,600 B2 | 5/2012 | Dokka | |
| 8,216,786 B2 | 7/2012 | Shiffman et al. | |
| 8,241,651 B2 | 8/2012 | Lahann | |
| 8,338,115 B2 | 12/2012 | Adler | |
| 8,360,973 B2 | 1/2013 | Bazin | |
| 8,484,155 B2 | 7/2013 | Yamaguchi | |
| 8,871,920 B2 | 10/2014 | Purschke | |
| 9,457,071 B2 | 10/2016 | Hide | |
| 9,518,265 B2 | 12/2016 | Hohlig | |
| 9,709,576 B2 | 7/2017 | Hide | |
| 9,732,348 B2 | 8/2017 | Cauchard | |
| 9,902,961 B2 | 2/2018 | Dausse | |
| 9,976,145 B2 | 5/2018 | Jarosch | |
| 9,996,674 B2 | 6/2018 | Segman | |
| 10,001,496 B2 | 6/2018 | Jung | |
| 10,231,531 B2 | 3/2019 | Witchell | |
| 10,308,943 B2 | 6/2019 | Erickson et al. | |
| 10,650,289 B2 | 5/2020 | Szegedy | |
| 10,676,396 B2 | 6/2020 | Johannsmann et al. | |
| 10,994,919 B2 | 5/2021 | Hochberg et al. | |
| 11,016,094 B2 | 5/2021 | Gilboa-geffen | |
| 11,172,873 B2 * | 11/2021 | Purwar ............... | A45D 44/005 |
| 2002/0065452 A1 | 5/2002 | Bazin | |
| 2002/0150287 A1 | 10/2002 | Kobayashi | |
| 2002/0183988 A1 | 12/2002 | Skaanning | |
| 2003/0014324 A1 | 1/2003 | Donovan | |
| 2004/0236592 A1 | 11/2004 | Aleles | |
| 2006/0085274 A1 | 4/2006 | Sottery | |
| 2006/0149151 A1 | 7/2006 | Ladjevardi | |
| 2006/0178904 A1 | 8/2006 | Aghassian | |
| 2007/0054261 A1 | 3/2007 | Sherman | |
| 2007/0058858 A1 | 3/2007 | Harville | |
| 2008/0097814 A1 | 4/2008 | Koustoumbardis | |
| 2008/0152600 A1 | 6/2008 | Huang et al. | |
| 2010/0106679 A1 | 4/2010 | Yamaguchi | |
| 2010/0254581 A1 | 10/2010 | Neeser | |
| 2011/0016001 A1 | 1/2011 | Schieffelin | |
| 2012/0041282 A1 | 2/2012 | Nichol | |
| 2012/0190627 A1 | 7/2012 | Delattre | |
| 2012/0320191 A1 | 12/2012 | Meschkat | |
| 2013/0323242 A1 | 12/2013 | Everett | |
| 2013/0332451 A1 | 12/2013 | Camplejohn et al. | |
| 2014/0018634 A1 | 1/2014 | Baumann | |
| 2014/0028822 A1 | 1/2014 | Khadavi | |
| 2014/0081095 A1 | 3/2014 | Krishnan | |
| 2014/0216492 A1 | 8/2014 | Magri | |
| 2014/0378810 A1 | 12/2014 | Davis | |
| 2015/0045631 A1 | 2/2015 | Ademola | |
| 2015/0217465 A1 | 8/2015 | Krenik | |
| 2015/0329863 A1 | 11/2015 | Cauchard et al. | |
| 2015/0353933 A1 | 12/2015 | Miyakawa et al. | |
| 2016/0061602 A1 | 3/2016 | Fessi | |
| 2016/0326530 A1 | 11/2016 | Dausse et al. | |
| 2017/0004558 A1 | 1/2017 | Abramowitz | |
| 2017/0107515 A1 | 4/2017 | Eberly et al. | |
| 2017/0166894 A1 | 6/2017 | Demock et al. | |
| 2017/0270593 A1 | 9/2017 | Sherman | |
| 2018/0040052 A1 | 2/2018 | Robinson | |
| 2018/0040053 A1 | 2/2018 | Robinson | |
| 2018/0116583 A1 | 5/2018 | Cook | |
| 2018/0140248 A1 | 5/2018 | Chandra | |
| 2018/0223285 A1 | 8/2018 | Hohlig | |
| 2018/0225673 A1 | 8/2018 | Dubey | |
| 2018/0235535 A1 | 8/2018 | Cook | |
| 2018/0247365 A1 | 8/2018 | Cook | |
| 2018/0253866 A1 | 9/2018 | Jain | |
| 2018/0318719 A1 * | 11/2018 | Ma ....................... | G06N 3/006 |
| 2018/0349979 A1 | 12/2018 | Robinson | |
| 2019/0035149 A1 | 1/2019 | Chen | |
| 2019/0048348 A1 | 2/2019 | Velasquez | |
| 2019/0048349 A1 | 2/2019 | Velasquez et al. | |
| 2019/0112593 A1 | 4/2019 | Penner | |
| 2019/0183232 A1 | 6/2019 | Knuebel et al. | |
| 2019/0209077 A1 * | 7/2019 | Charraud ............. | A61B 5/0077 |
| 2019/0350514 A1 | 11/2019 | Purwar | |
| 2019/0355115 A1 | 11/2019 | Niebauer | |
| 2019/0355119 A1 | 11/2019 | Hu | |
| 2020/0000697 A1 | 1/2020 | Velasquez et al. | |
| 2020/0002703 A1 | 1/2020 | Velasquez | |
| 2020/0055659 A1 | 2/2020 | Hochberg | |
| 2020/0196936 A1 | 6/2020 | Blank | |
| 2020/0221995 A1 | 7/2020 | Mathiaszyk et al. | |
| 2020/0286152 A1 | 9/2020 | Thiagarajan et al. | |

(56) References Cited

U.S. PATENT DOCUMENTS

| | | |
|---|---|---|
| 2020/0330353 A1 | 10/2020 | Velasquez et al. |
| 2020/0367961 A1 | 11/2020 | Podmore et al. |
| 2021/0059754 A1 | 3/2021 | Kasprzak |
| 2021/0097595 A1 | 4/2021 | Senior, III et al. |
| 2021/0106696 A1 | 4/2021 | Dalma-weiszhausz et al. |

FOREIGN PATENT DOCUMENTS

| | | |
|---|---|---|
| DE | 102018207560 A1 | 11/2019 |
| EP | 3627444 A1 | 3/2020 |
| FR | 3020465 A1 | 10/2015 |
| GB | 490384 A | 8/1938 |
| JP | 2004354207 A | 12/2004 |
| JP | 3163309 U | 9/2010 |
| JP | 2017009426 A | 1/2017 |
| JP | 6138696 B2 | 5/2017 |
| JP | 2018041434 A | 3/2018 |
| JP | 2019212073 A | 12/2019 |
| JP | 6647438 B1 | 1/2020 |
| JP | 2020171428 A | 10/2020 |
| KR | 101456942 B1 | 11/2014 |
| KR | 102047237 B1 | 12/2019 |
| RU | 2306921 C1 | 9/2007 |
| TW | I670047 B | 9/2019 |
| WO | 0187245 A2 | 11/2001 |
| WO | 0191602 A2 | 12/2001 |
| WO | 02083737 A1 | 10/2002 |
| WO | 2011085727 A1 | 7/2011 |
| WO | 2017207455 A1 | 12/2017 |
| WO | 2018173073 A1 | 9/2018 |
| WO | 2018202065 A1 | 11/2018 |
| WO | 2019177451 A1 | 9/2019 |
| WO | 2021050928 A1 | 3/2021 |

OTHER PUBLICATIONS

Shinobu Nagase et al. "Changes in structure and geometric properties of human hair by aging", Journal of Cosmetic Science, vol. 60, Nov./Dec. 2009, pp. 637-648.
Wisuwat Sunhem et al., "An Approach to Face Shape Classification for Hairstyle Recommendation", 8th International Conference on Advanced Computational Intelligence, Feb. 14-16, 2016, pp. 390-394.
"How C-Lab is Preparing for a Future Full of Potential—Part 1: C-Lab Inside", Samsung Newsroom, 5 pgs, Jan. 2, 2020.
"Jack Florek '17 presents at ACS in San Francisco", Emmanuel College, retrieved from http://gerdonlab.blogs.emmanuel.edu/2017/04/04/jack-florek-17-presents-acs-san-francisco/, Oct. 15, 2018, 6 pages.
All Office Actions; U.S. Appl. No. 16/587,224.
All Office Actions; U.S. Appl. No. 16/413,920.
All Office Actions; U.S. Appl. No. 16/441,749.
All Office Actions; U.S. Appl. No. 16/953,385.
All Office Actions; U.S. Appl. No. 17/230,121.
All Office Actions; U.S. Appl. No. 17/326,505.
Aram Huvis Co., Ltd, Aram Huvis' skin & Hair Analysis System, APM (Aramo Professional Microscope), Jun. 15, 2017, 1 pg.
Artificial Intelligence in Skin and Hair Diagnnostic Technology, year 2020, 1 pg.
Bawazer et al., "Efficient Selection of Biomineralizing DNA Aptamers Using Deep Sequencing and Population Clustering", ACS Nano, vol. 8, No. 1, 2014, pp. 1-10.
Benhabiles et al., "Deep learning based detection of hair loss levels from facial images", year 2019, 6 pgs.
Chang et al., "A mobile device-based hairy scalp diagnosis system using deep learning techniques", IEEE 2nd Global Conference on Life Sciences and Technologies, year 2020, pp. 145-146.
Database WPI, XP002785798, Week 201649, 2017, Thomson Scientific, London GB, AN 2016-20069A, 1 pg.
Eifler, Electronic Nose-Based Fusarium Detection and Deoxynivalenol Aptamer Development, Dissertation, Jul. 2014, 106 pages.
Fujii et al.,"Pesticide vapor sensing using an aptamer, nanopore, and agarose gel on a chip", Lab on a Chip, vol. 17, No. 14, 2017, pp. 2421-2425.
Gao et al., "Post-Selex optimization of aptamers", Analytical and Bioanalytical Chemistry, Springer, vol. 408, No. 17, 2016, pp. 4567-4573.
Geron, "Introducing Capsule Networks", O'Reilly, https://www.oreilly.com/content/introducing-capsule-networks/, Feb. 6, 2018, pp. 1-7.
H. Shih, "A precise automatic system for the hair assessment in hair-care diagnosis applications", Skin Research and Technology, 2015, pp. 500-507.
Hasegawa et al., "Methods for Improving Aptamer Binding Affinity", Molecules, vol. 21, No. 4, 2016, pp. 1-15.
Huang et al., "A cloud-based intelligent skin and scalp analysis system", Dec. 2018, 5 pages.
Hurot et al., "Bio-Inspired Strategies for Improving the Selectivityand Sensitivity of Artificial Noses: A Review", Sensors, vol. 20, No. 6, 2020, pp. 1-28.
Illuminate, powerpoint presentation, property of Aduivo Diagnostics PVT Ltd, 10 pgs.
Infusing Technology to advance the growth of the Hair Care Industry, Hair Analysis—KritiKal, Year 2021, 4 pgs.
PCT Search Report and Written Opinion for PCT/US2019/032382; dated Jul. 31, 2019, 14 pages.
Janas et al., "The selection of aptamers specific for membrane molecular targets", Cellular & Molecular Biology Letters, vol. 16, No. 1, 2011, pp. 25-39.
John et al., "ANYL 154: DNA aptamers that bind with high affinity to hydroxyapatite", ACS National Meeting & Exposition; 253rd National Meeting of The American-Chemical-Society (ACS) On Advanced Materials, Technologies, Systems, and Processes, American Chemical So, vol. 253, Apr. 2017, p. ANYL154.
Komarova et al., "Selection, Characterization, and Application of ss DNA Aptamer against Furaneol", Molecules, vol. 23, No. 12, 2018, pp. 1-15.
Kuznetsov et al., "Aptamer based vanillin sensor using an ion-sensitive field-effect transistor", Microchimica Acta, vol. 185, No. 1, 2017, 26 pages.
Lee et al., "An intelligent hair and scalp analysis system using camera sensors and Norwood-Hamilton model", International Journal of Innovative Computing, Information and Control, vol. 14, No. 2, pp. 503-518, Apr. 2018.
Li et al., "VEGF induces proliferation of human hair follicle dermal papilla cells through VEGFR-2-mediated activation of ERK", Experimental Cell Research, vol. 318, No. 14, 2012, pp. 1633-1640.
Low et al., "DNA aptamers bind specifically and selectively to (1-3)-beta-d-glucans", Biochemical and Biophysical Research Communications, vol. 378, No. 4, 2009, pp. 701-705.
Nonaka et al., "Screening and improvement of an anti-VEGF DNA aptamer", Molecules, vol. 15, No. 1, 2010, pp. 215-225.
Pillaiyar et al., "Downregulation of melanogenesis: drug discovery and therapeutic options", Drug Discovery Today, vol. 22, No. 2, Feb. 2017, pp. 282-298.
Ramos et al., "Female Pattern Hair Loss: A Clinical and Pathophysiological Review", ABD: Anais Brasileiros De Dermatologia, vol. 90, No. 4, Jul.-Aug. 2015, pp. 1-29.
Schwartz et al., "The role of oxidative damage in poor scalp health: ramifications to causality and associated hair growth", International Journal of Cosmetic Science, vol. 37, No. Suppl. 2, 2015, pp. 9-15.
Shibata et al., "The cell wall galactomannan antigen from Malassezia furfur and Malassezia pachydermatis contains -1,6-linked linear galactofuranosyl residues and its detection has diagnostic potential", Microbiology, vol. 155, No. 10, 2009, pp. 3420-3429.
Su et al., "An Intelligent Scalp Inspection and Diagnosis System for Caring Hairy Scalp Health", pp. 508-509, 2018.
Tang et al., "Improved detection of deeply invasive candidiasis with DNA aptamers specific binding to (1-3)-[beta]-D-glucans from Candida albicans", European Journal of Clinical Microbiology & Infectious diseases, vol. 35, No. 4, 2016, pp. 587-595.

(56) References Cited

OTHER PUBLICATIONS

Unpublished U.S. Appl. No. 16/953,385, filed Nov. 20, 2020, to Supriya Punyani et al.

Unpublished U.S. Appl. No. 17/230,121, filed Apr. 14, 2021, to first inventor Supriya Punyani et. al.

Unpublished U.S. Appl. No. 17/326,505, filed May 21, 2021, to first inventor Supriya Punyani et. al.

Velegraki et al., "Malassezia Infections in Humans and Animals: Pathophysiology, Detection and Treatment", PLOS Pathogens, vol. 11, No. 1, Jan. 2015, pp. 1-6.

Wan-Jung Chang et al., "Scalp Eye: A Deep Learning Based Scalp Hair Inspection and Diagnosis System for Scalp Health", IEEE Access, Jul. 21, 2020, vol. 8, Digital Object Identifier 10.1109/Access.2020.3010847, pp. 134826-134837.

Wang et al., "Development and experimental evaluation of machine-learning techniques for an intelligent hairy scalp detection system", Applied Sciences, Year 2018, 28 pgs.

"Connected scalp advisor shows root of the problem" URL Link: https://www.youtube.com/watch?v=Y-oAEiCO1-g, Jan. 9, 2019.

\* cited by examiner

SYSTEMS AND METHODS FOR HAIR ANALYSIS

FIELD OF THE INVENTION

The present application relates generally to hair analysis systems and methods comprising: (a) a step to capture an image of a user at an image capture unit and to send the image from the image capture unit to a hair analysis unit; (b) a step to analyze the user's hair condition at hair analysis unit, based on the image from the image capture unit by using a deep neural network, and to provide an analysis result to a display unit; and (c) a step to display at a display unit the analysis result to the user. The present invention provides the system and the method with an improved sensitivity.

BACKGROUND OF THE INVENTION

Assessing hair condition is of interest in order to understand, for example, the degree of damages caused to keratinaceous fibers. Such assessment is also of interest in order to demonstrate the efficacy of treatments used for preventing and/or repairing keratinaceous fiber damages. Several attempts for assessing keratinaceous fiber damages, using different methods and/or sensors, have already been reported.

For example, WO 201732637 from UNILEVER, which discloses a method of and system for recommending one or more products to a consumer from a plurality of products, the system comprising: a user interface; and a processor configured to: provide a list of questions for the consumer at the user interface, each question having a defined set of answers; calculate a consumer score for each question using the answer chosen by the consumer at the user interface; calculate a recommendation score for each question, using the consumer score; and select the one or more products for recommendation to the consumer based on the recommendation score.

Another example includes JP3163309U from UNILEVER, which discloses a device for assessing personal skin or hair and then recommending the proper personal care products based on the assessment. The device comprises a casing, a camera, at least two light emitting diodes, an actuator, an information storage unit and a transmitting unit, wherein the casing is provided with a plurality of holes, the camera is contained in the casing and provided with a lens guided to receive light passing through the first hole of the holes, each light emitting diode is positioned on the lateral surface of the lens, the actuator is used for manually switching on the light emitting diodes and extends out of the casing through the second hole of the holes, and the transmitting unit positioned in the casing is used for wirelessly transmitting image information obtained by the camera.

Also, assessing hair style is of interest, and several attempts have already been reported. For example, WO 200899938 from KAO discloses a hair image display method and display device, wherein the method comprises the steps of: selecting a hair area from a hair image; performing an edge detection on the hair area to calculate an edge image; performing representation processing on the edge image to calculate a representative value image; calculating direction differences between the edge image and the representative value image; and rendering the direction differences of respective pixels in color or grayscale to display a direction difference image, or rendering the correlation lengths of respective pixels in an edge direction image in color or grayscale to display a bundle width image, or determining the curvatures of the respective pixels in the edge direction image to form a curvature image. This makes it possible to display directions straying from a flow, bundles of hairs in the same flow, and the state of curls in hair styling clearly, and to facilitate evaluations of the hair styling.

However, these methods, systems and assessments rely on predetermined information about the hair physical properties and appearance and thus fails to generalize for real life hair conditions.

Accordingly, there is a need for a system and method of evaluating consumer hair conditions with improved sensitivity to assess real life hair conditions, and providing such evaluation results; a customized product recommendation based on the evaluation result; and a customized hair style recommendation based on the evaluation result.

SUMMARY OF THE INVENTION

The present invention is directed to a hair analysis system comprising: a) a camera to capture an image of a user and to send the image to a hair analysis processor; b) the hair analysis processor: to analyze the user's hair condition based on the image by using a model that is trained using a plurality of images of users that each feature one or more micro features of a respective user's hair and to provide an analysis result to a display wherein the analysis result is at least one of the following: the analyzed hair condition; a hair prediction based on the analyzed hair condition; a hair product recommendation based on the analyzed hair condition; a hair product usage recommendation based on the analyzed hair condition; and a hair style recommendation based on the analyzed hair condition; c) the display to display the analysis result to the user.

The present invention is also directed to a hair analysis method comprising: a) capturing an image of a user as captured by a camera and sending the image to a hair analysis processor; b) analyzing the user's hair condition at the hair analysis processor, based on the image from the camera by using a model that is trained using a plurality of images of users that each feature one or more micro features of a respective user's hair, and to provide an analysis result to a display wherein the analysis result is at least one of the following: the analyzed hair condition; a hair prediction based on the analyzed hair condition; a hair product recommendation based on the analyzed hair condition; a hair product usage recommendation based on the analyzed hair condition; and a hair style recommendation based on the analyzed hair condition; c) displaying at the display the analysis result to the user.

The system and method of analyzing user's hair conditions with improved sensitivity to assess real life hair conditions, and providing such analysis results. By the use of a model in the method and the system to provide a user with hair analysis of how the user looks from an image in which both the user's hair and face are shown, the system uses very little image pre-processing reducing dependence on predetermined information about the image and helps to generalize, thus, evaluating consumer hair conditions with improved sensitivity to assess real life hair conditions.

BRIEF DESCRIPTION OF THE DRAWINGS

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate various embodiments described herein, and together with the description serve to explain the principles and operations of the claimed subject matter.

DETAILED DESCRIPTION OF THE INVENTION

Figure 1:
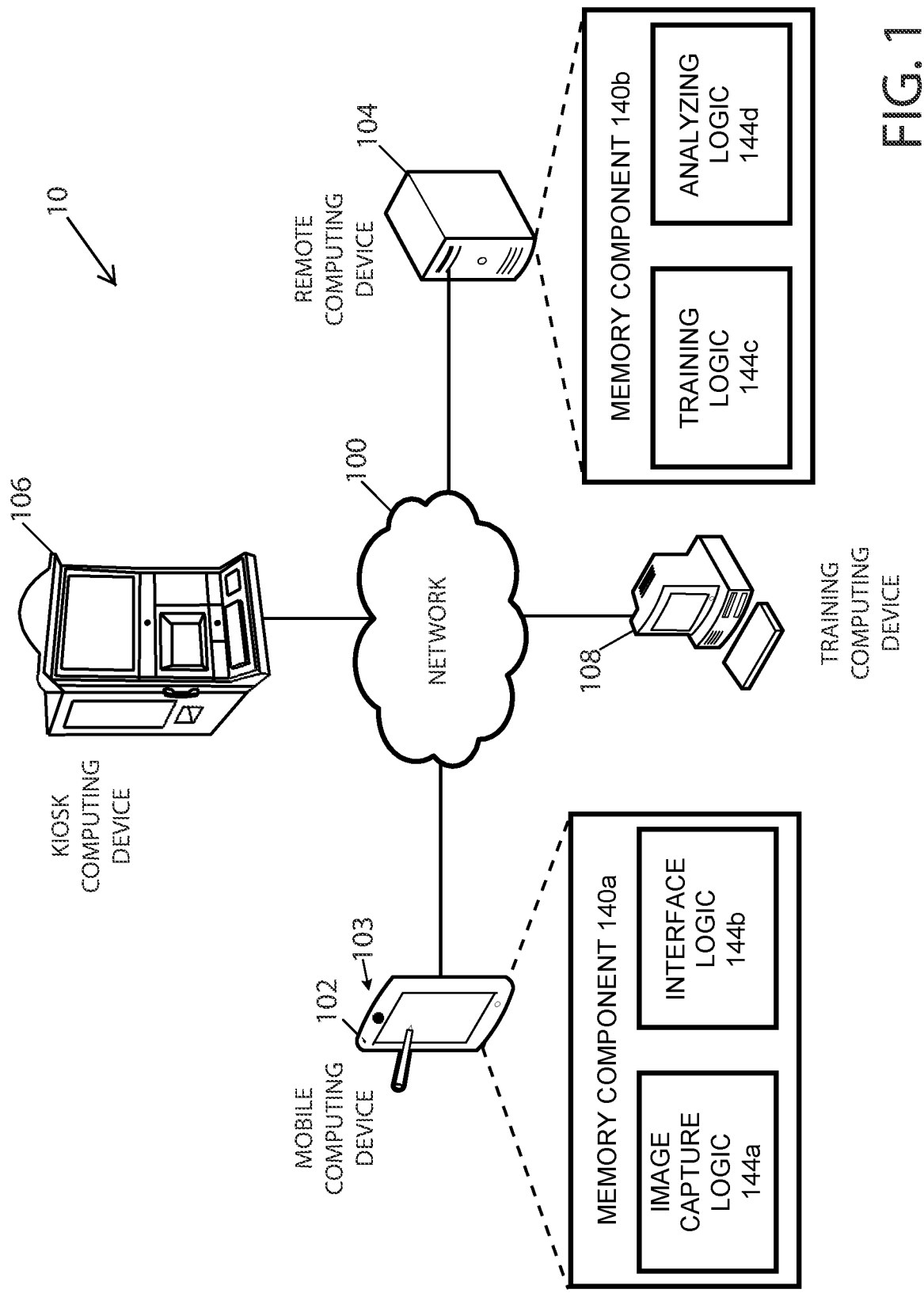
FIG. 1 depicts a computing environment for providing customized product recommendations, according to embodiments described herein

"Deep neural network" is a type of feed-forward artificial neural network with multiple layers of neurons or units that build a hierarchy of learned features or concepts representing the input. Examples of these DNN could be Convolutional Neural Networks (CNN) or Deep Capsule Networks (DCN).

"Coupled," when referring to various components of the system herein, means that the components are in electrical, electronic, and/or mechanical communication with one another.

"Data augmentation" means altering data associated with a training image or other image to create additional samples for the image.

"Feature vector" means a series of features that contain information describing one or more characteristics of an object in a digital image. Each feature in the feature vector is typically represented by one or more numbers, but any suitable indicator may be used, as desired (letters, symbols, colors, etc.)

"Image capture device" means a device such as a digital camera capable of capturing an image of a user;

"Macro features" are relatively large bodily features found on or near the face of a human. Macro features include, without limitation, face shape, ears, eyes, mouth, nose, hair, and eyebrows.

"Micro features" are relatively small hair presentation features e.g. frizz, shine, volume, and visual cues to assess hair condition. Micro features do not include macro features.

"Model" herein refers to a mathematical equation, algorithm, or computer software used to predict, describe, or imitate a set of circumstances, a system, or a naturally occurring phenomenon.

"Selfie" refers to a digital photograph of a person taken by that person, another person, or an automated image capture system (e.g., photo booth or security camera).

"Hair age" means the age of a user's hair calculated by the system herein, based on a captured image.

"Target hair age" means a hair age that is a predetermined number of years less than the hair age.

"User" herein refers to a person who uses at least the features provided herein, including, for example, a device user, a product user, a system user, and the like.

Image Capture Unit

The image capture unit is used to capture an image of a user and to send the image to a hair analysis unit.

The image of the user herein is an image showing user's hair and face. In the image, it is preferred that the ratio of the face size to the image size ratio is around 20% to 70%, so that the image shows more than 70% of the outline of the hair, preferably 80%, more preferably 90%, still more preferably 95% of the outline of the hair. The image herein can be anything such as selfie and video.

The image capture unit can be connected to the hair analysis unit by wired or wireless connection.

Q&A User Interface Unit

This unit, which is optionally included into the system and/or method of the present invention, is to provide a question for the user at the user interface; to receive an answer from the user; and to send the answer to a hair analysis unit.

In some embodiment, this unit can provide a list of questions for the consumer at the user interface, wherein each question having a defined set of answers; to send the answer chosen by the consumer at the user interface to the hair analysis unit.

Questions herein are, for example, those relating to use's hair conditions, those relating to user's habit associated with hair; those relating to user's product preference, those relating to user's hair style preference, those relating to user's geographic information, those relating to user's gender, those relating to user's age; those relating to user's life style.

The answer can be utilized for providing hair analysis result at the hair analysis unit. The answer can be sent to the hair analysis unit in any form, for example, can be sent as it is, or can be sent as a score calculated from the answer.

The question and answer interface unit can be connected with the hair analysis unit by wired or wireless connection. The question and answer interface unit can be connected with the image capture unit by wired or wireless connection, or can be independent from the image capture unit, or can be physically located together with the image capture unit, for example, within the same mobile computing device.

Hair Analysis Unit

The hair analysis unit is to analyze the user's hair condition based on the image by using a deep neural network; and to provide an analysis result to a display unit wherein the analysis result is at least one of the followings: the analyzed hair condition; hair prediction based on the analyzed hair condition; hair product recommendation based on the analyzed hair condition; hair product usage recommendation based on the analyzed hair condition; and hair style recommendation based on the analyzed hair condition.

Preferably, the hair analysis unit additionally preprocess the image, wherein preprocessing comprises: determining an anchor feature on the image and altering the image to place the anchor feature in a predetermined position.

Preferably, the hair condition analysis can be made in the hair analysis unit by the steps comprising:

Preprocessing;

Applying a deep neural network (DNN) to extract micro and micro features including both face and hair features;

Optionally comparing the features to a standard evaluation data; and

Providing analyzed hair conditions.

Hair conditions to be analyzed herein are at least one of the followings: Frizz; Volume, especially Volume lift at the roots; Freshness or Cleanliness; Moisture; Curliness; Length; Manageability; Damage; Shine; Hair age; and Hair health, preferably, at least one of the followings: Frizz; Volume, especially Volume lift at the roots; Freshness or Cleanliness; Moisture; Curliness; Length; Manageability; Damage; Hair age; and Hair health, more preferably at least one of the followings: Frizz; Volume, especially Volume lift at the roots; Freshness or Cleanliness; Moisture; Manageability; Damage; Hair age; and Hair health.

For the analysis of these hair conditions, the present invention can provide improved sensitivity by incorporation of facial features, compared to the analysis only based on hair features in the image.

Hair prediction, hair product recommendation, hair product usage recommendation, and hair style recommendation are all based on such analyzed hair condition.

The hair analysis unit can be connected with the display unit by wired or wireless connection.

Display Unit

The display unit is to display the analysis result to the user, wherein the analysis result is at least one of the followings: the analyzed hair condition; hair prediction based on the analyzed hair condition; hair product recommendation based on the analyzed hair condition; hair product usage recommendation based on the analyzed hair condition; and hair style recommendation based on the analyzed hair condition.

Preferably, the display showing the hair product recommendation and/or hair product usage recommendation, also shows an option for the user to purchase the product.

The analysis result can be shown, for example, by numerical data such as absolute values, relative values, indexes, and/or colors with or without indications. Alternatively or concurrently, the analyzed hair condition can be shown, for example, by cartoon, and/or by indication and/or highlight on the image to show the area for improvement.

The display unit can be physically located together with the image capture unit and/or the Q&A user interface unit, for example, within the same mobile computing device. Alternatively, the display unit can be located separately from any of them.

EXAMPLES

The systems and methods herein preferably use a trained a deep neural network such as a CNN or DCN, to analyze hair conditions of a user by analyzing a captured image of the user. The CNN comprises multiple layers of neuron collections that use the same filters for each pixel in a layer. Using the same filters for each pixel in the various combinations of partially and fully connected layers reduces memory and processing requirements of the system.

In some instances, the system may include a preprocessing stage followed by a stage for CNN or DCN training and image analysis. During preprocessing, one or more facial and hair features common to most users, such as eyes, forehead, cheeks, nose, under eye region, outer eye region, nasolabial folds, lips, hair color, hair type e.g. curly, straight, or wavy, hair length, chronological age, lighting environment, hair falling back or hair in front, facial pose and portions of the images adjacent these features, ("anchor features"), in a received image may be detected. The system may detect the anchor feature(s) using known edge detection techniques, shape detection techniques, and the like. Based on the location of the anchor feature(s), the image may be scaled and rotated to make the image substantially level and with the anchor feature(s) arranged in a predetermined position in the final image. In this way, training images can be consistently aligned, thus providing more consistent training and analysis. The image may then be cropped to a predetermined area of pixels as input for further processing.

Preprocessing may also include image normalization. For example, global contrast normalization may be utilized to standardize the training images (and/or images of users) to address the variability that could be introduced by real life selfie capture condition.

In some instances, data augmentation may be performed to create additional samples from an inputted image. The additional samples are used to train the CNN or DCN to tolerate variation in input images. This helps improve the accuracy of the model. In other words, the CNN or DCN is able to extract the information & relationships of important features necessary for a suitable analysis in spite of differences in, for example, the way people take photographs, the conditions in which photos are taken, and the hardware used to take a photo. The additional samples generated by data augmentation can also force the CNN or DCN to learn to rely on a variety of features for hair condition analysis rather than one particular feature, and may prevent over-training of the CNN or DCN. Some non-limiting examples of data augmentation include randomly enlarging or shrinking the image, randomly rotating the image in a clockwise or counter-clockwise direction, randomly cropping the image, and/or randomly changing the saturation and/or exposure of the image. In some instances, the image data may be augmented by subjecting the input image to random vertical dropout, in which a random column of pixels is removed from the image.

The CNN or DCN herein may be trained using a deep learning technique, which allows the CNN or DCN to learn what portions of an image contribute to skin, face features, hair characteristics, etc., much in the same way as a mammalian visual cortex learns to recognize important features in an image. In some instances, the CNN training may involve using mini-batch stochastic gradient descent (SGD) with Nesterov momentum (and/or other algorithms). An example of utilizing a stochastic gradient descent is disclosed in U.S. Pat. No. 8,582,807.

DCN is composed of many capsules. A capsule is a small group of neurons that learns to detect a particular object (e.g., a rectangle) within a given region of the image, and it outputs a vector (e.g., an 8-dimensional vector) whose length represents the estimated probability that the object is present, and whose orientation (e.g., in 8D space) encodes the object's pose parameters (e.g., precise position, rotation, etc.). Much like a regular neural network, a DCN is organized in multiple layers. The capsules in the lowest layer are called primary capsules: each of them receives a small region of the image as input (called its receptive field), and it tries to detect the presence and pose of a particular pattern, for example a rectangle. Capsules in higher layers, called routing capsules, detect larger and more complex objects, such as boats. The primary capsule layer may be implemented using a few regular convolutional layers. For example, two convolutional layers could be used that output 256 6×6 features maps containing scalars. These feature maps could be reshaped to get 32 6×6 maps containing 8-dimensional vectors. Finally, a squashing function may be applied to ensure these vectors have a length between 0 and 1 (to represent a probability).

The capsules in the next layers may also try to detect objects and their pose using an algorithm called routing by agreement. The routing-by-agreement algorithm may involve a few iterations of agreement-detection+routing-update (this may happen for each prediction, not just once, and not just at training time).

In some instances, the DNN may be trained by providing an untrained DNN with a multitude of captured images to learn from. In some instances, the DNN can learn to identify portions of an image that contribute to a particular hair condition through a process called supervised learning. "Supervised learning" generally means that the DNN is trained by analyzing images in which the hair attributes of the person in the image is predetermined. Depending on the accuracy desired, the number of training images may vary from a few images to a multitude of images (e.g., hundreds or even thousands) to a continuous input of images (i.e., to provide continuous training).

The systems and methods herein utilize a trained DNN that is capable of accurately analyzing hair condition of a user for a wide range of hair types and styles. To provide analyzed hair condition, an image of a user is forward-propagating through the trained DNN. The DNN analyzes the image and identifies portions of the image that contribute to the hair condition. The DNN then uses the identified portions to analyze hair condition of the user.

In some instances, the DNN analysis, analyzed hair condition and/or target condition, optionally in conjunction with habits and practices input provided by a user, can be used to help provide a hair prediction, hair case product recommendation, hair product usage recommendation and/or hair style recommendation.

FIG. 1 depicts a system 10 for capturing an image of a user, analyzing the image, and providing a customized product recommendation. The system 10 may include a network 100, which may be embodied as a wide area network (such as a mobile telephone network, a public switched telephone network, a satellite network, the internet, etc.), a local area network (such as wireless-fidelity, Wi-Max, ZigBee™, Bluetooth™, etc.), and/or other forms of networking capabilities. Coupled to the network 100 are a mobile computing device 102, a remote computing device 104, a kiosk computing device 106, and a training computing device 108.

The mobile computing device 102 may be a mobile telephone, a tablet, a laptop, a personal digital assistant and/or other computing device configured for capturing, storing, and/or transferring an image such as a digital photograph. Accordingly, the mobile computing device 102 may include an image capture device 103 such as a digital camera and/or may be configured to receive images from other devices. The mobile computing device 102 may include a memory component 140a, which stores image capture logic 144a and interface logic 144b. The memory component 140a may include random access memory (such as SRAM, DRAM, etc.), read only memory (ROM), registers, and/or other forms of computing storage hardware. The image capture logic 144a and the interface logic 144b may include software components, hardware circuitry, firmware, and/or other computing infrastructure, as described herein. As described in more detail below, the image capture logic 144a may facilitate capturing, storing, preprocessing, analyzing, transferring, and/or performing other functions on a digital image of a user. The interface logic 144b may be configured for providing one or more user interfaces to the user, which may include questions, options, and the like. The mobile computing device 102 may also be configured for communicating with other computing devices via the network 100.

The remote computing device 104 may also be coupled to the network 100 and may be configured as a server (or plurality of servers), personal computer, mobile computer, and/or other computing device configured for creating and training a convolutional neural network capable of analyze hair conditions of a user by identifying portions of a captured image that contribute to a particular hair condition. The remote computing device 104 may include a memory component 140b, which stores training logic 144c and analyzing logic 144d. The training logic 144c may facilitate creation and/or training of the DNN, and thus may facilitate creation of and/or operation of the DNN. For example, the DNN may be stored as logic 144c, 144d in the memory component 140b of a remote computing device 104. The analyzing logic 144d may cause the remote computing device 104 to receive data from the mobile computing device 102 (or other computing device) and process the received data for providing analyzed hair conditions, product recommendation, hair style recommendation, etc.

The system 10 may also include a kiosk computing device 106, as illustrated in FIG. 1. The kiosk computing device 106 may operate similar to the mobile computing device 102, but may also be able to dispense one or more products and/or receive payment in the form of cash or electronic transactions. In some instances, the kiosk computing device 106 may also be configured to facilitate training of the DNN, as described in more detail below with regard to the training computing device 108.

A training computing device 108 may be coupled to the network 100 to facilitate training of the DNN. For example, a trainer may provide one or more digital images of a face or skin or hair to the DNN via the training computing device 108. The trainer may also provide information and other instructions to inform the DNN which assessments are correct and which assessments are not correct. Based on the input from the trainer, the DNN may automatically adapt, as described in more detail below.

It should be understood that while the kiosk computing device 106 is depicted as a vending machine type of device, this is merely an example. Some embodiments may utilize a mobile device that also provides payment and/or production dispensing. Similarly, the kiosk computing device 106, the mobile computing device 102, and/or the training computing device 108 may be utilized for training the DNN. As a consequence, the hardware and software depicted for the mobile computing device 102 and the remote computing device 104 may be included in the kiosk computing device 106, the training computing device 108, and/or other devices. Similarly, a hardware and software may be included in one or more of the mobile computing device 102, the remote computing device 104, the kiosk computing device 106, and the training computing device 108.

It should also be understood that while the remote computing device 104 is depicted in FIG. 1 as performing the deep neural network processing, this is merely an example. The deep neural network processing may be performed by any suitable computing device, as desired.

Figure 2:
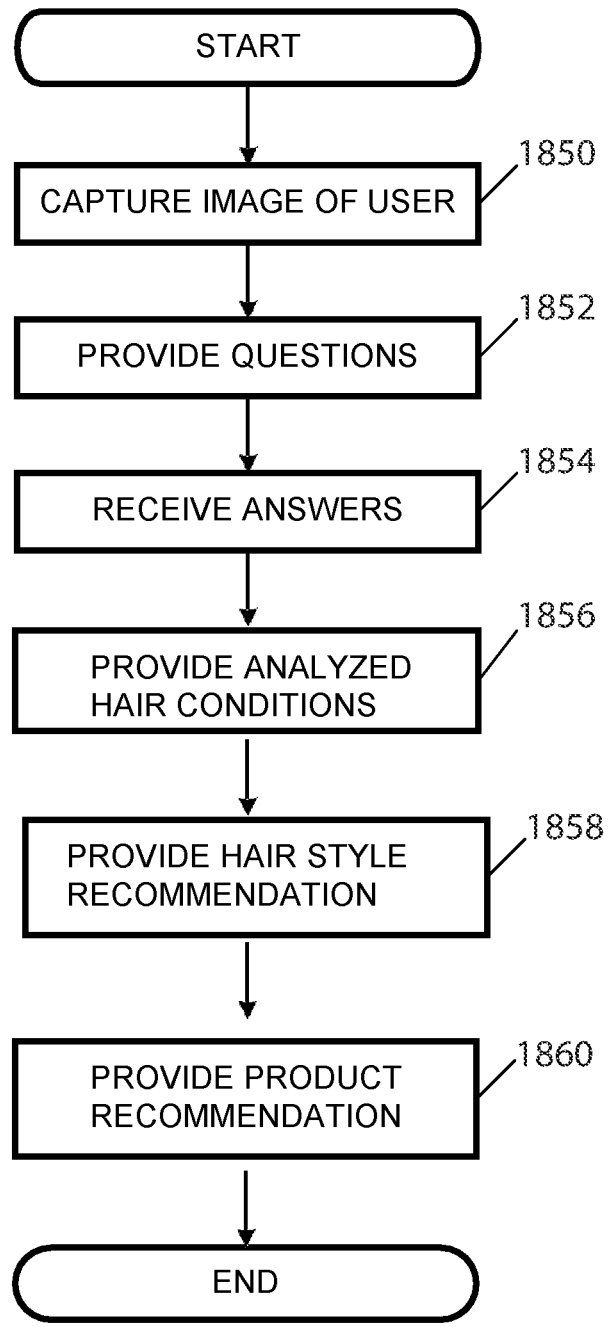
FIG. 2 depicts a flowchart for providing customized product recommendations, according to embodiments described herein.

FIG. 2 depicts a flowchart for providing customized product recommendations, according to embodiments described herein. In block 1850, an image of a user may be captured. In block 1852, questions may be provided to the user. In block 1854, answers to the questions may be received from the user. In block 1856, analyzed hair condition may be provided to the user. In block 1858, a customized hair style recommendation may be provided to the user. In block 1860, a customized product recommendation may be provided to the user.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair analysis system comprising:
    (a) a camera to capture an image of a user and to send the image to a hair analysis processor;
    (b) the hair analysis processor: to analyze the user's hair condition based on the image by using a model that is trained using a plurality of images of users that each feature one or more of the following features of a respective user's hair: frizz, cleanliness, moisture, curliness, length, damage, or shine; and to provide an analysis result to a display wherein the analysis result is at least one of the following:
    the analyzed hair condition;
    a hair prediction based on the analyzed hair condition;
    a hair product recommendation based on the analyzed hair condition;
    a hair product usage recommendation based on the analyzed hair condition; or
    a hair style recommendation based on the analyzed hair condition; and
    (c) the display to display the analysis result to the user.

2. The system of claim 1, wherein the model comprises at least one of: a deep neural network or a Convolutional Neural Network.

3. The system of claim 2, wherein the deep neural network is a Deep Capsule Network.

4. The system of claim 1, wherein the display further shows an option for the user to purchase a product.

5. The system of claim 1, wherein the hair condition to be analyzed is at least one of the following: Frizz; Volume; Freshness or Cleanliness; Moisture; Curliness; Length; Manageability; Damage; Shine; Hair age; or Hair health.

6. The system of claim 1, wherein the system further comprises a question and answer (Q&A) user interface unit to provide a question for the user at the Q&A user interface; to receive an answer from the user; and to send the answer to the hair analysis processor.

7. The system of claim 6, wherein the answer is utilized to provide the analysis result.

8. A hair analysis method comprising:
    (a) capturing an image of a user as captured by a camera and sending the image to a hair analysis processor;
    (b) analyzing the user's hair condition at the hair analysis processor, based on the image from the camera by using a model that is trained using a plurality of images of users that each feature one or more of the following features of a respective user's hair: frizz, cleanliness, moisture, curliness, length, damage, or shine; and to provide an analysis result to a display wherein the analysis result is at least one of the following:
    the analyzed hair condition;
    a hair prediction based on the analyzed hair condition;
    a hair product recommendation based on the analyzed hair condition;
    a hair product usage recommendation based on the analyzed hair condition; or
    a hair style recommendation based on the analyzed hair condition; and
    (c) displaying at the display the analysis result to the user.

9. The method of claim 8, wherein the model comprises at least one of: a deep neural network or a Convolutional Neural Network.

10. The method of claim 9, wherein the deep neural network is a Deep Capsule Network.

11. The method of claim 8, wherein the display further shows an option for the user to purchase a product.

12. The method of claim 8, wherein the hair condition to be analyzed is at least one of the followings: Frizz; Volume; Freshness or Cleanliness; Moisture; Curliness; Length; Manageability; Damage; Shine; Hair age; or Hair health.

13. The method of claim 8 further comprising displaying a question and answer user interface to provide a question for the user; and receiving an answer from the user; and sending the answer to the hair analysis processor.

14. The method of claim 13, wherein the answer is utilized for providing the analysis result.

* * * * *